United States Patent
Bril et al.

(10) Patent No.: US 6,613,785 B2
(45) Date of Patent: Sep. 2, 2003

(54) USE OF GLUCOSE UPTAKE ENHANCER FOR REDUCING POST-ISCHEMIC INJURY OF THE HEART

(75) Inventors: Antoine Michel Alain Bril, Rennes (FR); Robin Edwin Buckingham, Welwyn Garden City (GB); Nassirah Khandoudi, Rennes (FR)

(73) Assignees: Smithkline Beecham plc, Middlesex (GB); Glaxosmithkline Laboratoires Pharmaceutiques, Cedex (FR)

( * ) Notice: Subject to any disclaimer, the term of this patent is extended or adjusted under 35 U.S.C. 154(b) by 0 days.

(21) Appl. No.: 10/348,456

(22) Filed: Jan. 21, 2003

(65) Prior Publication Data

US 2003/0109554 A1 Jun. 12, 2003

Related U.S. Application Data

(63) Continuation of application No. 09/744,118, filed as application No. PCT/GB99/02358 on Jul. 21, 1999, now abandoned.

(30) Foreign Application Priority Data

Jul. 21, 1998 (GB) ................................. 9815871
Jul. 21, 1998 (GB) ................................. 9815872

(51) Int. Cl.$^7$ .......................................... A61K 31/425
(52) U.S. Cl. ..................................................... 514/369
(58) Field of Search ........................................ 514/369

(56) References Cited

U.S. PATENT DOCUMENTS 5,968,960 A    10/1999  Schwartz .................... 514/369

FOREIGN PATENT DOCUMENTS

| EP | 0 306 228 A1 | 8/1998 |
|----|--------------|--------|
| JP | 5-202042 | 10/1993 |
| WO | WO 94/05659 | 3/1994 |
| WO | WO 97/46238 | 12/1997 |
| WO | WO 98/08531 | 3/1998 |
| WO | WO 99/25346 | 5/1999 |
| WO | WO 99/43326 | 9/1999 |
| WO | WO 99/59586 | 11/1999 |

OTHER PUBLICATIONS

Shimabukuro, et al., "Cardioprotective Effects of Troglitazone in Strptozotocin–Induced Diabetic Rats", (1996), Metabolism, vol. 45, No. 9, pp. 1168–1173.

J. Sternon, "La Prise En Charge Du Post–Infarctus", (1997), Revue Medicale De Bruxelles, 18:4, pp. 286–292, Ref.: 28, XP00085687.

Horikoshi, et al., "Thiazolidines for treatment of complications of diabetes", Database Chemabs 'Online!, Chemical Abstracts Service, STN Database accession No. 119:262523, XP002124805, Abstract & JP 05 202042 A, (1993).

Bähr, et al., "Acuete and chronic effects of troglitazone (CS–045) on isolated rat ventricular cardiomyocytes", (1996), Diabetologia, 39, pp. 766–774.

Yokoyama, et al., "Glutathione reductase activity potentiator containing troglitazone", Database Chemabs 'Online!, Chemical Abstracts Service, STN Database accession No. 128:248588, XP002124804, Abstract & WO 98/10760, (1998).

*Primary Examiner*—Raymond Henley, III
(74) *Attorney, Agent, or Firm*—Kathryn L. Sieburth; Mary MCCarthy; Charles M. KInzig

(57) ABSTRACT

A method for reducing post-ischaemic injury of the heart and/or improving the functional recovery of the heart following myocardial ischaemia which method comprises administration of an effective, non-toxic amount of a glucose uptake enhancer to a human or non-human mammal in need thereof.

10 Claims, 2 Drawing Sheets

USE OF GLUCOSE UPTAKE ENHANCER FOR REDUCING POST-ISCHEMIC INJURY OF THE HEART

This is a continuation of U.S. application Ser. No. 09/744,118, filed Jan. 19, 2001, now abandoned, which is a 371 of PCT/GB99/02358 filed Jul. 21, 1999.

This invention relates to a novel method for preventing or reducing post-ischaemic injury of the heart, in particular myocardial infarction or for improving the functional recovery of the heart following myocardial ischaemia.

Cardiovascular disease is a leading cause of mortality in adult diabetics of both Type 1 and Type 2 etiologies. The underlying presence of cardiovascular disease in diabetes means not only that the likely incidence of myocardial infarction is higher in the diabetic population but that its occurrence carries a substantially greater risk of mortality for diabetics than non-diabetics. European Patent Application. Publication Number 0,306,228 relates to certain thiazolidinedione derivatives disclosed as having antihyperglycaemic and anti-hyperlipidaemic activity. One particular thiazolidinedione disclosed in EP 0306228 is 5-[4-[2-(N-methyl-N-(2-pyridyl)amino)ethoxy]benzyl]thiazoiidine-2,4-dione (hereinafter 'Compound (I)'). WO94/05659 discloses certain salts of Compound (I) including the maleate salt at example 1 thereof.

Compound (I) is an example of a class of antihyperglycaemic agents known as 'insulin sensitisers.'. In particular Compound (I) is a thiazolidinedione insulin sensitiser. Thiazolidinedione insulin sensitisers include compounds comprising a 2,4-thiazolidinedione moiety.

European Patent Applications, Publication Numbers: 0008203, 0139421, 0032128, 0428312, 0489663, 0155845, 0257781, 0208420, 0177353, 0193256, 0319189, 0332331, 0332332, 0528734, 0508740; International Patent Application, Publication Numbers 92/18501, 93/02079, 93,22445 and U.S. Pat. Nos. 4,687,777, 5,104,888 and 5,478,852, also disclose certain thiazolidinedione insulin sensitisers.

Another series of compounds generally recognised as having insulin sensitiser activity are those typified by the compounds disclosed in International Patent Applications, Publication Numbers WO93/21166 and WO94/01420. These compounds are herein referred to as 'acyclic insulin sensitisers'. Other examples of acyclic insulin sensitisers are those disclosed in U.S. Pat. No. 5,232,945 and International Patent Applications, Publication Numbers WO92/03425 and WO91/19702.

Examples of other insulin sensitisers are those disclosed in European Patent Application, Publication Number 0533933, Japanese Patent Application Publication Number 05271204 and U.S. Pat. No. 5,264,451.

The above mentioned publications are incorporated herein by reference.

It is suggested by Shimabukuro et al (Diabetes 44[Suppl 1]:797 (Abstract) 1995) that long term treatment with the thiazolidinedione, troglitazone, preserves cardiac function of the diabetic heart. Also, Eckel et al (Diabetes, 46[Suppl 1]: 575 (Abstract) 1997) have suggested that chronic exposure to troglitazone may exert a cardioprotective effect by increasing glucose supply to the myocytes of the diabetic heart.

It is now surprisingly indicated that the acute administration of Compound (I) exerts a cardioprotective effect on the diabetic heart and is therefore effective at preventing or reducing post-ischaemic injury, such as myocardial infarction. The acute administration of Compound (I) is also indicated to improve the functional recovery of the diabetic heart following myocardial ischaemia.

In addition, and perhaps more surprisingly, it is indicated that administration, especially acute administration, of Compound (I) exerts a particularly effective cardioprotective effect on the non-diabetic heart.

Accordingly, the present invention provides a method for reducing post-ischaemic injury of the heart, in particular myocardial infarction, which method comprises administration, especially acute administration, of an effective, non-toxic amount of a glucose uptake enhancer to a human or non-human mammal in need thereof.

The invention also provides a method for improving the functional recovery of the heart following myocardial ischaemia which method comprises administration, especially acute administration, of an effective, non-toxic amount of a glucose uptake enhancer to a human or non-human mammal in need thereof.

In one particular aspect the invention provides a glucose uptake enhancer, such as Compound (I) or a tautomeric form thereof or a pharmaceutically acceptable derivative thereof, for use in reducing post-ischaemic injury of the heart, in particular myocardial infarction or for use in improving the functional recovery of the heart following myocardial ischaemia.

Certain of the human or non-human mammals may be suffering from diabetes mellitus or a related disorder. Particularly, the diabetes mellitus is Type 1 diabetes mellitus. Particularly, the diabetes mellitus is Type 2 diabetes mellitus.

A suitable glucose uptake enhancer is an insulin sensitiser.

A suitable glucose uptake enhancer is a thiazolidinedione.

Suitable thiazolidinediones are those disclosed in the above mentioned publications.

A preferred thiazolidinedione is Compound (I), or the tautomeric form thereof, or a pharmaceutically acceptable derivative thereof.

Other suitable thiazolidinediones include (÷)-5-[[4-[(3,4-dihydro-6-hydroxy-2,5,7,8-tetramethyl-2H-1-benzopyran-2-yl)methoxy]phenyl]methyl]-2,4-thiazolidinedione (or troglitazone), 5-[4-[(1-methylcyclohexyl)methoxy]benzyl] thiazolidine-2,4-dione (or ciglitazone), 5-[4-[2-(5-ethylpyridin-2-yl) ethoxy] benzyl] thiazolidine-2,4-dione (or pioglitazone) or 5-[(2-benzyl-2,3-dihydrobenzopyran)-5-ylmethyl)thiazolidine-2,4-dione (or englitazone): or a pharmaceutically acceptable derivative thereof.

A suitable pharmaceutically acceptable derivative is a pharmaceutically acceptable salt or a pharmaceutically acceptable solvate, including a pharmaceutically acceptable solvate of a pharmaceutically acceptable salt.

Suitable pharmaceutically acceptable derivatives, including pharmaceutically acceptable salts and pharmaceutically acceptable solvates, of the glucose uptake enhancer, for example the thiazolidinediones, are as described in the above mentioned publications and standard reference texts such as the British and US Pharmacopoeias, Remington's Pharmaceutical Sciences (Mack Publishing Co.), Martindale The Extra Pharmacopoeia (London, The Pharmaceutical Press).

Suitable pharmaceutically acceptable salts of Compound (I) include those described in EP 0306228 and WO94/05659. A preferred pharmaceutically acceptable salt is a maleate.

Suitable pharmaceutically acceptable solvated forms of Compound (I) include those described in EP 0306228 and WO94/05659, in particular hydrates.

Certain of the glucose uptake enhancers, such as the thiazolidinediones, for example Compound (I), may exist in one of several tautomeric forms, all of which are encompassed by the method of the invention, either as individual tautomeric forms or as mixtures thereof.

Certain of the glucose uptake enhancers, such as the thiazolidinediones, for example Compound (I), may also contain chiral carbon atoms, and hence can exist in several stereoisomeric forms, all of which are encompassed by the method of the invention whether as individual isomers or as mixtures of isomers.

The glucose uptake enhancers, such as the thiazolidinediones, including the pharmaceutically acceptable derivatives thereof, are prepared using conventional methods; for example the thiazolidinediones are conveniently prepared according to the methods disclosed in the above mentioned publications: Thus Compound (I), or the tautomeric form thereof, or a pharmaceutically acceptable derivative thereof, such as a salt thereof or a pharmaceutically acceptable solvate thereof, may be prepared using the processes described in EP 0306228 and WO94/05659.

The above mentioned stereoisomeric forms, such as those of the thiazolidinediones, may be prepared and separated as required, according to known methods such as those disclosed in the above mentioned publications.

The above-mentioned feature of the acute administration of glucose uptake enhancer, especially of the thiazolidinediones such as Compound (I), is considered to comprise in its own right a further part of the present invention. Accordingly, the invention further provides a glucose uptake enhancer, such as a thiazolidinedione for example Compound (I) or a tautomeric form thereof or a pharmaceutically acceptable derivative thereof, for use as an acutely administerable therapeutic substrate.

The present invention also provides a glucose uptake enhancer, such as a thiazolidinedione for example Compound (I) or a tautomeric form thereof or a pharmaceutically acceptable derivative thereof, for use as an acutely administrable cardioprotective agent, especially for preventing or reducing post-ischaemic injury of the heart, in particular myocardial infarction.

The present invention also provides a glucose uptake enhancer, such as a thiazolidinedione for example Compound (I) or a tautomeric form thereof or a pharmaceutically acceptable derivative thereof, for acute administration for improving the functional recovery of the heart following myocardial ischaemia.

In all of the above-mentioned treatments, the glucose uptake enhancer such as Compound (I) or a tautomeric form thereof or a pharmaceutically acceptable derivative thereof, may be administered per se or, preferably, as a pharmaceutical composition also comprising a pharmaceutically acceptable carrier.

Accordingly, the present invention also provides a pharmaceutical composition comprising a glucose uptake enhancer, such as Compound (I) or a tautomeric form thereof or a pharmaceutically acceptable derivative thereof, and a pharmaceutically acceptable carrier wherein such composition is adapted for acute administration.

More particularly, the present invention provides a pharmaceutical composition for use as an acutely administerable cardioprotective agent, especially for preventing or reducing post-ischaemic injury of the heart, in particular myocardial infarction, which composition comprises a glucose uptake enhancer, such as Compound (I) or a tautomeric form thereof or a pharmaceutically acceptable derivative thereof, and a pharmaceutically acceptable carrier.

The invention further provides a pharmaceutical composition for acute administration for improving the functional recovery of the heart following myocardial ischaemia, which composition comprises a glucose uptake enhancer, such as Compound (I) or a tautomeric form thereof or a pharmaceutically acceptable derivative thereof, and a pharmaceutically acceptable carrier.

It is also envisaged that the acute cardioprotective effect of a glucose uptake enhancer would be useful for enhancing post-surgical recovery. Accordingly, the invention further provides a method for enhancing recovery after surgery, especially major surgery, for example cardiac surgery, which method comprises administration, generally acute administration, of an effective, non-toxic amount of a glucose uptake enhancer such as Compound (I), or a tauromeric form thereof or a pharmaceutically acceptable derivative thereof. Said administration of the glucose uptake enhancer may be before or after surgery. Particular patient groups include the elderly such as post-60 year age groups.

As used herein the term "pharmaceutically acceptable" embraces compounds, compositions and ingredients for both human and veterinary use: for example the term 'pharmaceutically acceptable salt' embraces a veterinarily acceptable salt.

As used herein "post-ischaemic injury of the heart" includes myocardial infarction and certain arrhythmias, especially due to myocardial infarction.

As used herein "improving the functional recovery of the heart" includes improving or restoring cardiac output and/or enhancing the recovery, especially the rate of recovery, of cardiac output.

As used herein "acute administration" or phases or terms used to convey an equivalent meaning to acute administration refer to a single administration of the medicament or the short term use. Short term use of a thiazolidinedione insulin sensitiser means a period of time less than that associated with an antihyperglycaemic effect. A suitable short term use period is 3–4 weeks.

As used herein "glucose uptake enhancer" means an agent which increases basal (insulin independent) or insulin-stimulated uptake of glucose into a cell.

In the method of the invention, the active medicaments are preferably administered in pharmaceutical composition form.

Usually the compositions are adapted for oral administration. However, they may be adapted for other modes of administration, for example parenteral administration, sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The compositions are preferably in a unit dosage form in an amount appropriate for the relevant daily dosage.

Suitable dosage regimens, including details of unit dosages, for the thiazolidinediones include those described in the above mentioned publications or in reference texts such as the British and US Pharmacopoeias, Remington's Pharmaceutical Sciences (Mack Publishing Co.), Martindale The Extra Pharmacopoeia (London, The Pharmaceutical Press).

The compositions are preferably in a unit dosage form in an amount appropriate for the relevant daily dosages. For example, for compound (I), unit doses suitably contain up to 12 mg of Compound (I).

In the acute treatment of the invention, the glucose uptake enhancer, such as Compound (I), or the tautomeric form thereof, or a pharmaceutically acceptable derivative thereof, is generally administered as a single dose. However, if required, additional doses may be administered to provide suitable short-term, non-chronic treatments, for example to prevent or reduce post-ischaemic injury, such as myocardial infarction, due to a subsequent ischaemic event and/or to prevent or reduce the severity of such an event and/or its reoccurrence.

In the above mentioned acute administration of glucose uptake enhancers, for example thiazolidinediones, dosages are envisaged to include higher doses than those associated with an anti-hyperglycaemic effect.

In a further aspect the treatment comprises the sequential administration or the co-administration of a thrombolytic agent, such as streptokinase, with the glucose uptake enhancer, such as Compound (I) or the tautomeric form thereof, or a pharmaceutically acceptable derivative thereof.

Accordingly, the invention also comprises a pharmaceutical composition comprising a glucose uptake enhancer, such as Compound (I) or the tautomeric form thereof, or a pharmaceutically acceptable derivative thereof, and a thrombolytic agent, such as streptokinase, and a pharmaceutically acceptable carrier.

The particular thrombolytic agent and its required dosage include those described in reference texts such as the British and US Pharmacopoeias. Remington's Pharmaceutical Sciences (Mack Publishing Co.), Martindale The Extra Pharmacopoeia (London, The Pharmaceutical Press). The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agent can be dissolved in the vehicle. To enhance the stability, the composition can be frozen after filling into the vial and the water removed under vacuum. Parenteral suspensions are prepared in substantially the same manner, except that the active compound may be suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions may contain from 0.1% to 99% by weight, preferably from 10–60% by weight, of the active material, depending upon the method of administration.

Compositions may, if desired, be in the form of a pack accompanied by written or printed instructions for use.

Finally, the cardioprotective effects, especially the acute cardioprotective effects, of a glucose uptake enhancer, such as Compound (I) or the tautomeric form thereof, or a pharmaceutically acceptable derivative thereof, are also considered to provide potential for use as a cardioplegic agent. Accordingly, the present invention also provides a glucose uptake enhancer, such as Compound (I) or the tautomeric form thereof, or a pharmaceutically acceptable derivative thereof for use as a cardioplegic agent, especially in cardioplegic solutions, to preserve cardiac function during surgery.

Particular uses of a cardioplegic agent include use in cardiac by-pass surgery. Particular uses of a cardioplegic agent include use in cardiac transplant surgery for maintaining cardiac viability.

The amount of active agent required for cardioplegic use will be provided by standard tests methods such as those described herein, for example cardioplegic solutions of Compound (I) are envisaged to contain between 0.01 $\mu$M and 10 $\mu$M of Compound (I).

In a further aspect, the invention also provides a pharmaceutical composition, adapted for use as a cardioplegic agent, which comprises a glucose uptake enhancer, such as Compound (I) or a tautomeric form thereof, or a pharmaceutically acceptable derivative thereof and a pharmaceutically acceptable carrier.

The compositions are prepared and formulated according to conventional methods, such as those disclosed in standard reference texts, for example the British and US Pharmaceopoeias, Remington's Pharmaceutical Sciences (Mack Publishing Co.), Martindale The Extra Pharmacopeia (London, The Pharmaceutical Press and Harry's Cosmeticology (Leonard Hill Books) or the above mentioned publications.

The cardioprotective effects of the invention may be identified by using test methods such as those provided hereinafter or those known in the art such as those disclosed in Khandoudi N, Bernard M, Cozzone P, Feuvray D (Intracellular pH and role of Na+/H+ exchange during ischaemia and reperfusion of normal and diabetic rat hearts. *Cardiovasc Res* 24:873–878, 1990) or in Khandoudi N, Laville MP. Bril A (Protective effect of the Sodium/Hydrogen exchange inhibitors during global low flow-ischemia. *J Cardiovasc Pharmacol* 28:540–546, 1996).

No adverse toxicological effects have been established for the compositions or methods of the invention in the above mentioned dosage ranges.

In the Tables shown below:

Table 1: shows baseline ventricular function of isolated working hearts from male Wistar rats: with vehicle or Compound (I) added to the perfusate preischaemia;

Table 2: shows baseline ventricular function of isolated working hearts from STZ-diabetic rats: with vehicle or Compound (I) added to the perfusate preiscaemia.

Figure 1:
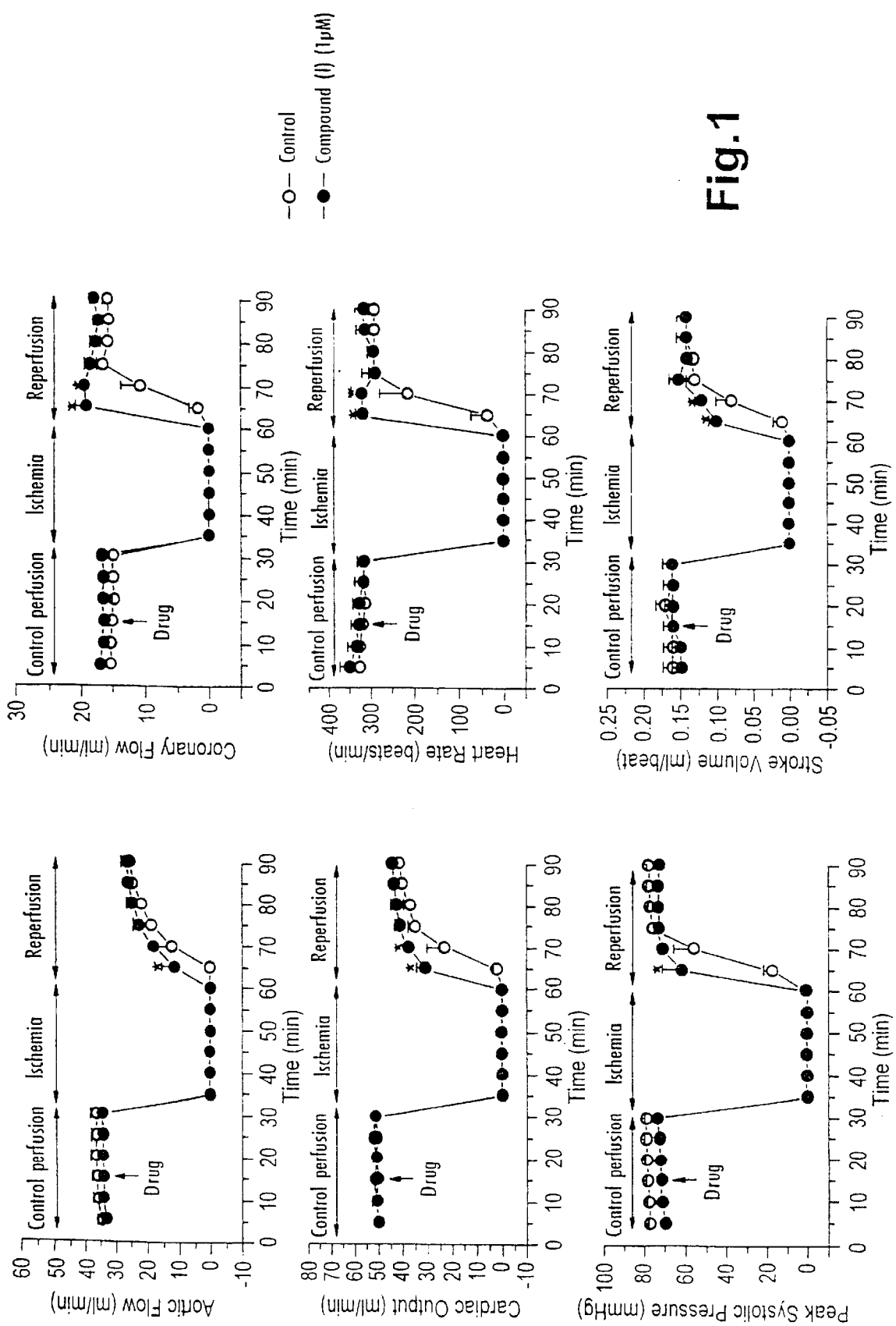
FIG. 1: shows the effect of Compound (I) on post-ischaemic functional impairment of normal Male Wistar rat working hearts.
Figure 2:
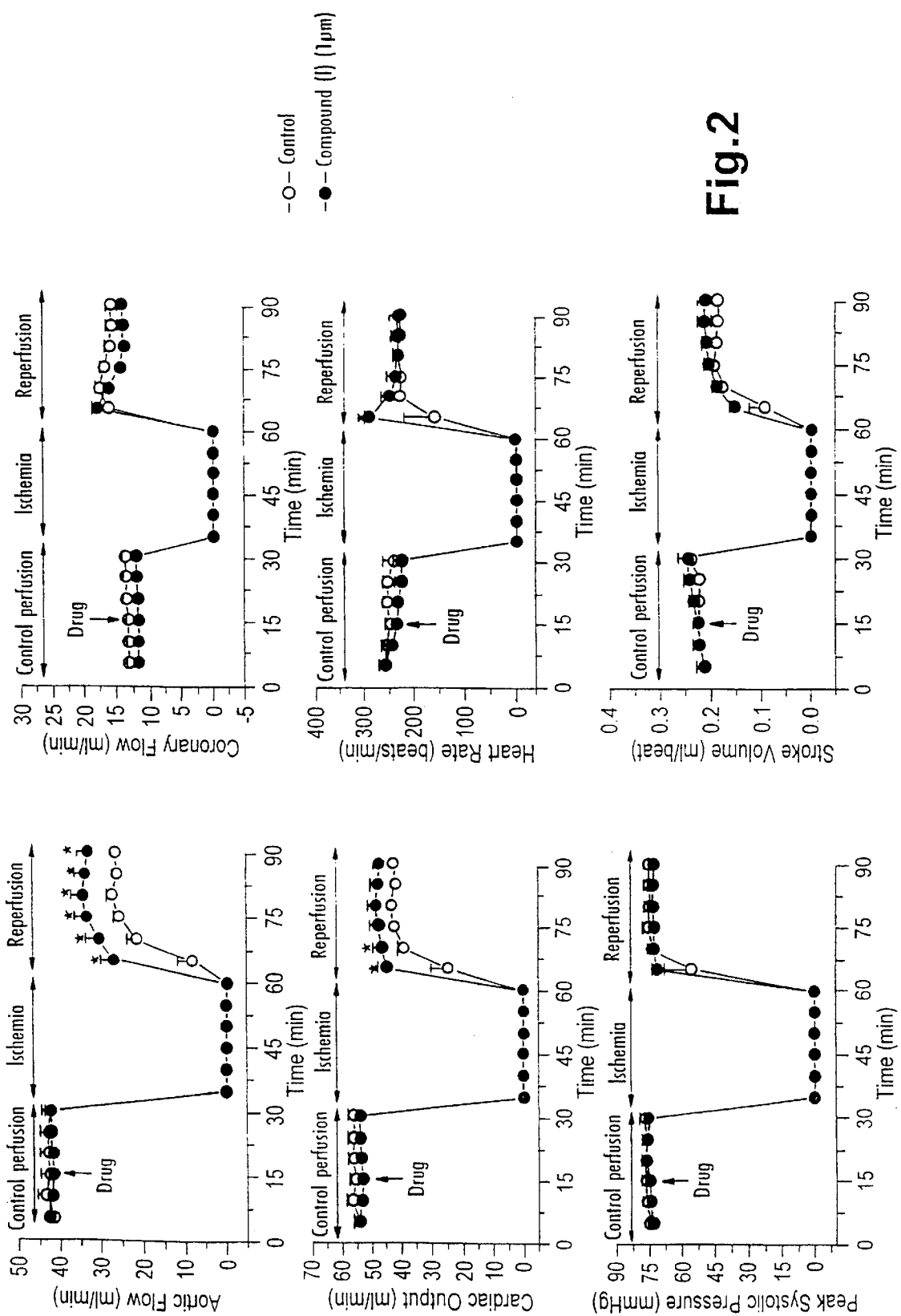
FIG. 2: shows the effect of Compound (I) on post-ischaemic functional impairment of STZ-diabetic male Wistar rat working hearts.

The following example illustrates the invention, but does not limit it in any way

MATERIALS & METHODS

Materials: Stock solutions of Compound (I) were prepared freshly in dimethylsulphoxide (DMSO) and further dilutions were made in the perfusion buffer. The maximum vehicle DMSO concentration was 0.001% which was without effect on any parameters when added by itself in control experiments. A solution of streptozotocin (STZ commercially available) was prepared in citrate buffer (40 mg/ml).

Test Systems: Male Wistar rats (Charles River; St Aubin lés Eibeuf, France), with a body weight ranging from 260 to 280 g were housed on a 12 h/12 h light-dark cycle with access to water and standard rat chow ad libitum. An acclimatisation period of at least one week was allowed prior to experiment.

Induction of experimental diabetes: Male Wistar rats weighing between 300 and 320 g were fasted overnight and made diabetic by a single intravenous injection of STZ 40 mg/kg body weight. The development of diabetes and its persistence were monitored by serial quantitative measurements of glucose in the urine with reagent strips. On the day of the experiment, the severity of diabetes was assessed by measuring glucose concentrations from blood samples collected at the time of heart excision. Only rats with plasma glucose levels exceeding 20 mM were considered diabetic and included in these experiments.

Experimental Procedures

Perfusion of isolated hearts: Rats were anaesthetized using thiopental sodium (50 mg/kg body weight intrapertioneally). Hearts from normoglycaemic and one-month STZ-induced diabetic rats, were quickly removed and immersed in ice-cold buffer to produce an immediate cessation of contractility. The aorta was dissected free and then mounted onto a cannula attached to a perfusion apparatus. Retrograde perfusion of the heart was started for 10 min by the Langendorff method and then switched to perfusion using the working-heart technique [16]. The perfusion fluid was Krebs-Henseleit buffer (pH 7.4) of the following composition (mM): NaCl 118, $NaHCO_3$ 23, KCl 4.7, $KH_2PO_4$ 1.2, $MgCl_2$ 1.2, $CaCl_2$ 1.25, glucose 11, pyruvate 2. The buffer was continuously gassed with a 95%$O_2$/5%$CO_2$ mixture and the entire system was thermoregulated at 37° C. The perfusate was not recirculated. Preload was held at a pressure of 15 cm $H_2O$ and afterload, as well as coronary perfusion pressure, were kept constant at 80 cm $H_2O$.

Measurement of cardiac function: Both heart rate (beat/min) and peak systolic pressure (mmHg) were monitored continuously via the fluid-filled side-arm on the aortic cannula connected to a pressure transducer (stratham P23Db) and recorded on a Gould pre-recorder (mode 8188.602). Aortic and coronary flows (ml/min) were measured by timed collection. Cardiac output (ml/min) was derived from the sum of the aortic and coronary flows. Stroke volume (ml/beat) was derived by dividing cardiac output by heart rate.

Induction of global ischaemia and re-perfusion: Total ischaemia was initiated by clamping the left atrium and the aortic perfusion tubes and reducing coronary flow to zero for 30 minutes. The hearts were then re-perfused at 37° C. in working heart mode and recovery of ventricular function was followed for 30 minutes. To investigate the action of Compound (I), this agent was added to the perfusate 15-min prior to the induction of ischaemia and then maintained throughout the re-perfusion phase.

Data Handling & Analysis: The data are presented as the mean=SEM. Statistical significance of differences was determined using Student's t-test. Differences with $p \leq 0.05$ were considered to be statistically significant.

Results: Baseline functional parameters for perfused normal male Wistar rat hearts ex vivo are shown in Table 1. In the perfusion system used here, at the constant outflow resistance, aortic flow reflects ventricular contractility [16]. The effects on cardiac function of inclusion of Compound (I) (1 $\mu$M) in the perfusate 15 min prior to xero-flow ischaemia (30 min) and subsequent re-perfusion, are shown in FIG. 1. The data demonstrate that recovery of post-ischaemic control hearts is relatively slow and not all functional parameters (e.g. cardiac output) return to pre-ischaemic levels, even after 30 min re-perfusion. Inclusion of Compound (I) in the perfusate prior to ischaemia significantly enhanced the rate of recovery of each of the functional indices. For example, inclusion of compound (I) (1 $\mu$M) in the perfusate for 15 min prior to, during ischaemia and during the subsequent re-perfusion phase, enhanced the recovery in cardiac output and heart rate.

Conclusions

The result of this study suggest that Compound (I) possesses protective properties of rapid onset in both normal and diabetic rat hearts subjected to zero-flow ischaemia in vitro.

1. Lehmann, J. M., Moore, L. B., Smith-Oliver, T. A., Wilkison, W. O., Willson, T. M. & Kliewer, S. A. 1995. An antidiabetic thiazolidinedione is a high affinity ligand for peroxisome proliferator activated receptor gamma (PPAR gamma). *J. Biol. Chem.,* 270 (22), 12953–12956.
2. Berger, J., Bailey, P., Biswas, C., Cullinan, C. A., Doebber, T. W., Hayes, N. S., Saperstein, R., Smith, R. G. & Leibowitz, M. D. 1996. Thiazolidinediones produce a conformational change in peroxisomal proliferator-activated receptor gamma: binding an activation correlate with antidiabetic actions in db/db mice. *Endocrinology,* 137 (10), 4189–4195.
3. Young, P. W., Buckle, D. R., Cantello, B. C. C., Chapman, H., Clapham, J. C., Coyle, P. J., Haigh, D., Hindley, R. M., Holder, J. C., Kallender, H., Latter, A. J., Lawrie, K. W. M., Mossakowska, D., Murphy, G. J., Cox, L. R. & Smith, S. A. 1998. Identification of high-affinity binding sites for the insulin sensitizer rosiglitazone (BRL 49653) in rodent and human adipocytes using a radioiodinated ligand for peroxisomal proliferator-activated receptor gamma, *J. Pharmacol. Exp. Ther.,* 284, 751–759.
4. Zhang, F., Sowers, J. R., Ram, J. L., Standley, P. R. & Peuler, J. D. 1994. Effects of pioglitazone on calcium channels in vascular smooth muscle. *Hypertension,* 24, 170–175.
5. Song, J., Walsh, M. F., Igwe, R., Ram, J. L., Barazi, M., Dominguez, L. J. & Sowers, J. R. 1997. Troglitazone reduces contraction by inhibition of vascular smooth muscle cell Ca 2+ currents and not endothelial nitric oxide production. *Diabetes,* 46, 659–664.
6. Nakamura, Y., Ohya, Y., Onaka, U., Fujii, K., Abe. I. & Fujishima, J. 1998. Inhibitory action of insulin-sensitizing agents on calcium channels in smooth muscle cells from resistance arteries of guinea-pig. *Br. J. Pharmac.*, 123, 675–682.
7. BRL-049653/RSD-100T6C/1. Differential effects of insulin-sensitizing agents troglitazone and rosiglitazone (BRL 49653) on Ca 2÷ and K÷ currents in rat vascular smooth muscle cells. Knock, G. A., Mishra, S. K. & Aaronson, P. I., June 1998.
8. Lee. K. & Boeden, P. 1997. Troglitazone inhibits type 2 K ATP channel activity and depolarises tolbutamide-sensitive neurones in the rat ventromedical hypothalamus. *Brain Research,* 751, 165–168.
9. Cairaldi, T. P., Gilmore, A., Olefsky, J. M., Goldberg, M. & Heidenreich, K. A. 1990. In vitro studies on the action of CS-045, a new antidiabetic agent, *Metabolism,* 39, 1056–1062.
10. Murano, K., Inoue, Y., Emoto, M., Kaku, K. & Kaneko, T. 1994. CS-045, a new antidiabetic agent, stimulates frustose-2,6-bisphosphate production in rat hepatocytes. *Eur. J. Pharmacol,* 254, 257–262.
11. Kellerer, M., Kroder, G., Tippmer, S., Berti, L., Liehn, R., Mosthaf, L. & Haring, H. 1994, troglitazone prevents glucose-induced insulin resistance of insulin receptor in rat-1 fibroblasts. *Diabetes,* 43, 447–453.
12. Bahr, M., Spelleken, M., Bock, M., Von Holtey, M., Kiehn, R. & Eckel, J., 1996. Acute and chronic effects of troglitazone (CS-045) on isolated rat ventricular cardiomyocytes. *Diabetologia,* 39, 766–774.
13. Eckel, J., Muller, H., Niggeman, J., Fujiwara, T., Horikoshi, H., Kiehn, R., 1997. Troglitzone-induced insulin-sensitizing in cardiac muscle of diabetic ZDF-rats correlates to inhibition and redistribution of membrane-associated PKC. *Diabetes,* 46 (suppl), 149A, 0575.
14. Ren, J., Dominquez, L. J., Sowers, J. R. & Davidoff, A. J. 1996. Troglitazone attenuates high-glucose-induced abnormalities in relaxation and intracellular calcium in rat ventricular myocotes. *Diabetes,* 45, 1822–1825.
15. Shimabukuro, M., Higa, S., Shinzato, T., Nagamine, F., Komiya, I. & Takasu, N. 1996. Cardioprotective effects of troglitazone in streptozotocin-induced diabetic rats. *Metabolism,* 45, 1168–1173.
16. Neely, J. R., Liebermeister, H., Battersby, E. J. & Morgan, H. E., 1967. Effect of pressure development on oxygen consumption by isolated rat heart. *Am. J. Physiol.,* 212, 804–814.
17. Garber, D. W. & Neely, J. R. 1983. Decreased myocardial function and myosin ATPase in hearts from diabetic rats. *Am. J. Physiol.,* 244, H586–H591.
18. Khandoudi, N., Bernard, M., Cozzone, P. & Feuvray, D. 1990. Intracellular pH and role of Na+/H÷ exchange during ischaemia and reperfusion of normal and diabetic rat hearts. *Cardiovasc. Res.,* 24, 873–878.

TABLE 1

|  | Male Wistar Rats: Control | Male Wistar Rats: Compound (1) (1 μM) |
|---|---|---|
| Aortic Flow (ml/min) | 36.5 ± 1.6 | 34.0 ± 0.7 |
| Coronary Flow (ml/min) | 15.0 ± 0.6 | 16.6 ± 0.6 |
| Cardiac Output (ml/min) | 52 ± 2 | 51 ± 1 |
| Peak Systolic Pressure (mmHg) | 79 ± 1 | 73 ± 1 |
| Stroke Volume (ml/beat) | 0.16 ± 0.01 | 0.16 ± 0.01 |
| Heart Rate (beats/min) | 314 ± 10 | 317 ± 15 |

TABLE 2

|  | Male Wistar STZ-Diabetic Rats: Control (n = 6) | Male Wistar STZ-Diabetic Rats: Compound (1) (1 μM) (n = 6) |
|---|---|---|
| Aortic Flow (ml/min) | 42.5 ± 1.7 | 42.3 ± 1.5 |
| Coronary Flow (ml/min) | 13.6 ± 0.5 | 12.1 ± 0.4 |
| Cardiac Output (ml/min) | 56.2 ± 2.0 | 54.4 ± 1.7 |
| Peak Systolic Pressure (mmHg) | 77 ± 2 | 76 ± 2 |
| Stroke Volume (ml/beat) | 0.24 ± 0.02 | 0.25 ± 0.01 |
| Heart Rate (beat/min) | 242 ± 19 | 225 ± 14 |

What is claimed is:

1. A method for reducing post-ischaemic injury of the heart and/or improving the functional recovery of the heart following myocardial ischaemia which method comprises administration of an effective, non-toxic amount of a glucose uptake enhancer to a human or non-human mammal in need thereof.

2. A method according to claim 1, wherein the glucose uptake enhancer is a thiazolidinedione.

3. A method according to claim 2, wherein the thiazolidinedione is 5-[4-[2-(N-methyl-N-(2-pyridyl)amino) ethoxy]benzyl]thiazolidine-2,4-dione, or the tautomeric form thereof, or a pharmaceutically acceptable derivative thereof.

4. A method according to claim 2, wherein the thiazolidinedione is selected from the group consisting of: (+)-5-[[4-[(3,4-dihydro-6-hydroxy-2,5,7,8-tetramethyl-2H-1-benzopyran-2-yl)methoxy]phenyl]methyl]-2,4-thiazolidinedione (or troglitazone), 5-[4-[(1-methylcyclohexyl)methoxy]benzyl] thiazolidine-2,4-dione (or ciglitazone), 5-[4-[2-(5-ethylpyridin-2-yl)ethoxy] benzyl] thiazolidine-2,4-dione (or pioglitazone) or 5-[(2-benzyl-2,3-dihydrobenzopyran)-5-ylmethyl)thiazolidine-2, 4-dione (or englitazone); or a pharmaceutically acceptable derivative thereof.

5. A method according to claim 3 wherein the pharmaceutically acceptable derivative is a pharmaceutically acceptable salt.

6. A method according to claim 5 wherein the pharmaceutically acceptable salt is a maleate.

7. A method according to claim 3 wherein the pharmaceutically acceptable derivative is a pharmaceutically acceptable solvate.

8. A method according to claim 7 wherein the pharmaceutically acceptable solvate is a hydrate.

9. A method according to claim 3 wherein the pharmaceutically acceptable derivative is a pharmaceutically acceptable solvate of a pharmaceutically acceptable salt.

10. A method according to claim 1 wherein the post-ischaemic injury of the heart is myocardial infarction.

* * * * *